United States Patent [19]

Sanderson

[11] 4,228,914
[45] * Oct. 21, 1980

[54] STERILIZED STORAGE CONTAINER

[76] Inventor: Roger S. Sanderson, 24662 Santa Clara Ave., Dana Point, Calif. 92629

[*] Notice: The portion of the term of this patent subsequent to Aug. 8, 1995, has been disclaimed.

[21] Appl. No.: 882,489

[22] Filed: Mar. 1, 1978

Related U.S. Application Data

[63] Continuation-in-part of Ser. No. 710,521, Aug. 2, 1976, abandoned, which is a continuation of Ser. No. 501,183, Aug. 28, 1974, abandoned.

[51] Int. Cl.³ .................. A61B 19/02; A61L 2/06; A61L 2/26; B65D 81/20
[52] U.S. Cl. ............................ 220/203; 206/1.5; 206/438; 206/524.8; 215/260; 220/209; 422/110; 422/111; 422/112; 422/295; 422/310
[58] Field of Search ............... 21/56, 78, 91–100, 21/104; 220/24, 203, 208, 209, 304, 363; 206/204, 438, 1.5, 524.8; 215/260; 49/2, 463; 53/11, 167; 236/92 R; 251/144, 61.1; 141/301; 422/26, 27, 38, 293, 295, 310, 296, 110–112

[56] References Cited

U.S. PATENT DOCUMENTS

| | | | |
|---|---|---|---|
| 2,024,511 | 12/1935 | Darling | 220/366 |
| 2,092,445 | 9/1937 | Doulgheridis | 215/355 |
| 2,097,585 | 11/1937 | Carson | 236/92 R |
| 2,489,989 | 11/1949 | Totman | 220/203 |
| 2,997,397 | 8/1961 | Doulgheridis | 215/355 |
| 3,061,196 | 10/1962 | Bauerlein | 251/144 |
| 3,468,471 | 9/1969 | Linder | 21/56 |
| 4,051,973 | 10/1977 | Botkin | 215/260 |
| 4,105,407 | 8/1978 | Sanderson | 422/26 |

FOREIGN PATENT DOCUMENTS 1642161  8/1970  Fed. Rep. of Germany ............ 21/104

*Primary Examiner*—Bradley R. Garris
*Attorney, Agent, or Firm*—Knobbe, Martens, Olson, Hubbard & Bear

[57] ABSTRACT

A container is disclosed with a valve opening at its bottom wall to permit steam to circulate into the container and to permit any condensation to drain from the container while the valve is open. The valve is closed by an expandable chamber in response to the pressure drop at the end of a sterilizing cycle. A valve controlling the flow of steam into the expandable chamber closes when subjected to the high temperature steam, thus capturing steam within the chamber. This steam expands when the pressure drops to close the valve in the container. The container lid and gasket permit steam to be withdrawn from the container but prevent air flow into the container. A vacuum created in the container at the end of the sterilizing cycle holds the container lid in place and holds the valve closed.

Also disclosed is a bimetallic spring valve which opens when steam is applied to a container and closes when the temperature drops as steaming ceases. The valve is biased closed at reduced temperature but opens when a vacuum is applied to the container exterior, thus permitting water vapor to be withdrawn.

1 Claim, 15 Drawing Figures

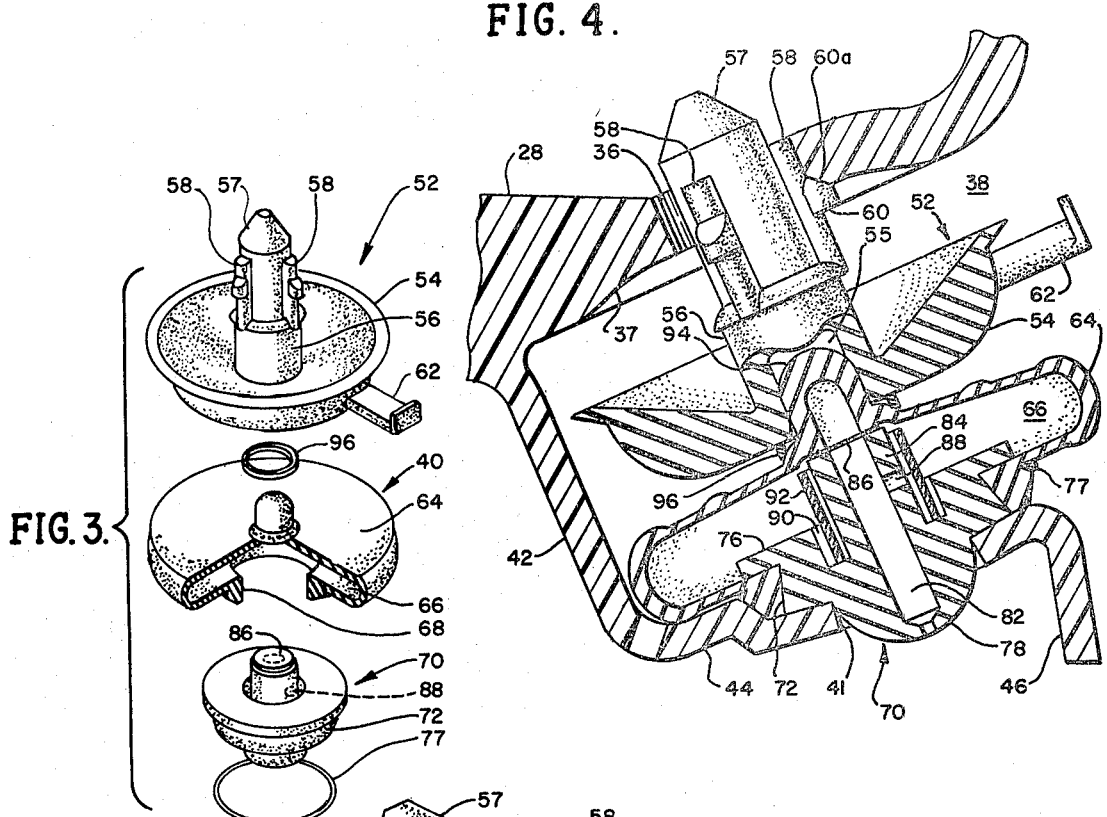
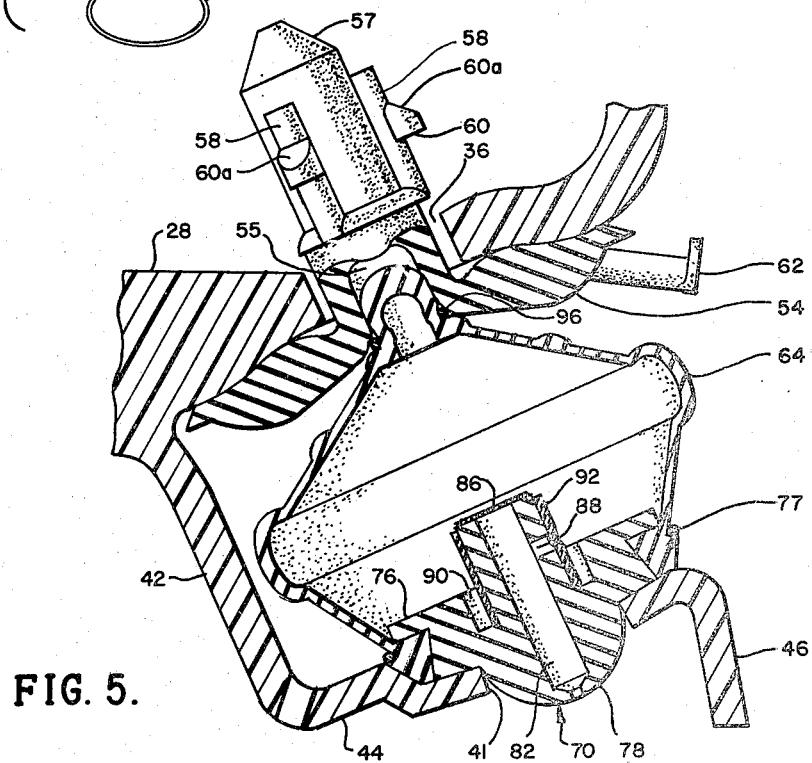

STERILIZED STORAGE CONTAINER

RELATED APPLICATIONS

This invention is a continuation-in-part of U.S. patent application, Ser. No. 710,521, filed Aug. 2, 1976, which is a continuation of application Ser. No. 501,183, filed Aug. 28, 1974, both applications now abandoned.

BACKGROUND OF THE INVENTION

This invention relates to an improved system for storing items while they are being sterilized, while they are being stored awaiting use, while they are in the process of being used, and after they have been used and are awaiting resterilization. The system is particularly useful in connection with the sterilization and storage of medical items, such as surgical instruments.

The most commonly used method for sterilizing surgical instruments and other medical items is to place them in towels which are enclosed in a sheet and taped shut for placing in a sterilizing autoclave. Sterilizing steam applied to the interior of the autoclave penetrates the porous materials surrounding the items to be sterilized. Moisture is removed by a vacuum drying cycle within a vacuum autoclave. When pressure is then returned to normal by admitting room air, unsterile air and lint from the towels are drawn into the center of the package. When the package is removed from the autoclave and cooled, additional room air circulates into the package. Thus, the items are immediately contaminated to some extent. If the package is not used immediately and placed in storage for a period of time, it must be returned to the autoclave for resterilization. It is estimated that two-thirds of sterilization work load in many hospitals is for items that were not used within the shelf life of the pack. This of course is an expensive and inefficient procedure which adds to the skyrocketing costs of medical treatment. Thus, a need exists for a practical and reliable system for handling sterile items and for maintaining sterility.

Some attempts have been made to improve the system for sterilizing medical items. However, all have fallen short of the mark such that the old approach of wrapping items in towels is still the method most widely used. U.S. Pat. No. 3,697,223—Kovalcik discloses a container in which items are to be sterilized and stored. However, the container is not adequately sealed after sterilization. U.S. Pat. No. 2,997,397—Doulgheridis and an earlier U.S. Pat. No. 2,092,445 of the same patentee disclose containers primarily for sterilizing food but are also said to be useful for surgical items. In those patents a vacuum is applied to a container which is open to initially withdraw the atmosphere within it, steam is applied, and the temperature of the stem melts a solder plug allowing a valve or cover for the container to close. Thus, the container is closed while still within the sterilizing environment but the sterilizing steam is trapped within it. This steam condenses in the container when cooled and is particularly undesirable for items which would be dry, such as surgical bandages.

U.S. Pat. No. 3,468,471 discloses a bag for containing items to be sterilized wherein the bag is porous at steam temperatures to permit steam to be applied to the contents of the bag but is not porous at lower temperatures. The bag also includes a temperature responsive valve which is open when the bag is in the autoclave so as to permit the steam to be rapidly withdrawn from the bag when a final vacuum is applied in the autoclave cycle. This valve closes to seal the container but not until the bag is removed from the autoclave and the temperature is dropped sufficiently to solidify an adhesive material. Thus, the bag is exposed to unsterile environment before being sealed. There are other patents dealing with the sterilization of food wherein a container is sealed in a sterile environment; however, steam or other atmosphere is deliberately maintained within the container and such arrangements are not suitable for medical items. Moreover, such containers are not automatically sealed in response to conditions of the environment surrounding the container.

Thus, a need still exists for a practical, easy to operate container useful for medical items, as well as other products, while such items are being sterilized, stored or used. Further, a need exists for such a container wherein maximum sterilization is obtained employing currently used autoclave apparatus. This is, of course, of vital importance for minimizing infections and other such medical problems encountered during surgury and post operative recovery. The present invention satisfies such need by providing maximum sterility consistent with that available by present-day autoclaves. Further, the system is practical and easy to operate by unskilled personnel, and current evidence indicates that it can greatly reduce the cost of sterilizing medical items in hospitals, doctors offices and other facilities employing autoclaves.

In accordance with the present invention, the items to be sterilized are placed within a container; and a sterilizing gaseous environment, such as high pressure steam, is applied to the container exterior, with the exterior in communication with the interior, for a period of time sufficiently long to sterilize the container and its contents. The application of the sterilizing environment is then discontinued and the pressure on the exterior of the container is reduced to allow the environment with the container to be withdrawn or escape from the container. The sterilized container is automatically sealed by means responsive to the environment surrounding the container so as to prevent fluid flow into the container before allowing the container to be exposed to an unsterilized environment.

Thus, when the container is placed within a vacuum autoclave, the container is open during the high pressure steaming operation, following which the steam is withdrawn by a final vacuum, and the container is automatically sealed while it is still within the autoclave and before unsterile exterior air is allowed to enter the autoclave. Thus, when the container is removed from the autoclave, its contents are sealed within a dry, essentially atmosphere-free container. With suitable material and gasketing, the container will remain in this condition for a long period of time in storage. The container contents remain sterile and air does not enter the container until it is opened in the operating room where the contents are to be used. Thus, exposure to unsterile environment is kept to an absolute minimum. The existence of the vacuum within the container of course produces a sound when the pressure is equalized and this gives the user assurance that the container was still sealed.

When the container is used in a non-vacuum (so-called gravity type) autoclave, most of the sterilizing steam escapes from the container when the steam phase is interrupted and the pressure is allowed to drop to room pressure. Some water vapor remains in the container at that time but the amount is quite small. When the container is sealed, and the temperature within the container drops to ambient temperature, this small amount of vapor condenses creating a relatively high vacuum within the container. This condensate can be accommodated by a quantity of dessicant to minimize the effect on the container contents. While use of the container in a vacuum type autoclave is preferable, there are a large number of the gravity type autoclaves in use and the system described provides the best sterility possible with such equipment.

In one form of the container, a valve is provided in a container wall which is normally closed but opens in response to steam temperatures so that steam applied to the exterior of the container can enter the container. After the steaming phase of the autoclave cycle and a reduction in temperature, the valve will once more automatically close, while the container is still within the autoclave and before room air is admitted to the autoclave. In addition, the valve is pressure responsive to act as a check valve so that when the pressure on the interior of the container exceeds that on the exterior, the valve will open but the valve will prevent flow into the container. Thus, in a vacuum autoclave, the sterilizing steam can be exhausted through the valve even after the valve has been initially closed by the drop in temperature which occurred when the steaming phase is completed. In one such arrangement, a bimetallic spring loaded valve is utilized which is both temperature responsive and pressure responsive.

In another arrangement disclosed herein, a valve remains open until near the end of a sterilizing cycle and is then closed in response to the falling pressure at the end of the sterilizing cycle. The closing means is triggered by an earlier rise in the temperature when steam is applied. This arrangement is claimed more specifically in a co-pending U.S.A. patent application, Ser. No. 821,042, filed Aug, 1, 1977.

An advantage of the arrangements disclosed is that the automatic operation of the closing of the container is independent of the duration of the sterilizing phase of a cycle. Thus, the containers remain open during this sterilizing to insure adequate sterilizing. This is particularly important with loads having considerable mass that must be heated to sterilizing temperatures. With loads of considerable mass, such as a quantity of medical instruments, there may be condensation of steam when it strikes the cooler instruments. To make certain that the condensate is not trapped within the container, the valve may be located at the bottom of the container to permit drainage until the valve is closed after the sterilizing phase is completed.

For a more thorough understanding of the invention refer now to the following detailed description and drawings in which:

FIG. 3 is an exploded perspective view of the container valve and valve closing mechanism;

FIG. 4 is an enlarged cross-sectional view of the container valve and valve closing mechanism shown on the container before being actuated by the sterilizing cycle;

FIG. 5 is a cross-sectional view of the structure of FIG. 4 after the valve has been moved into sealing position on the container valve seat by the expandable chamber forming the valve closing mechanism;

Figure 1:
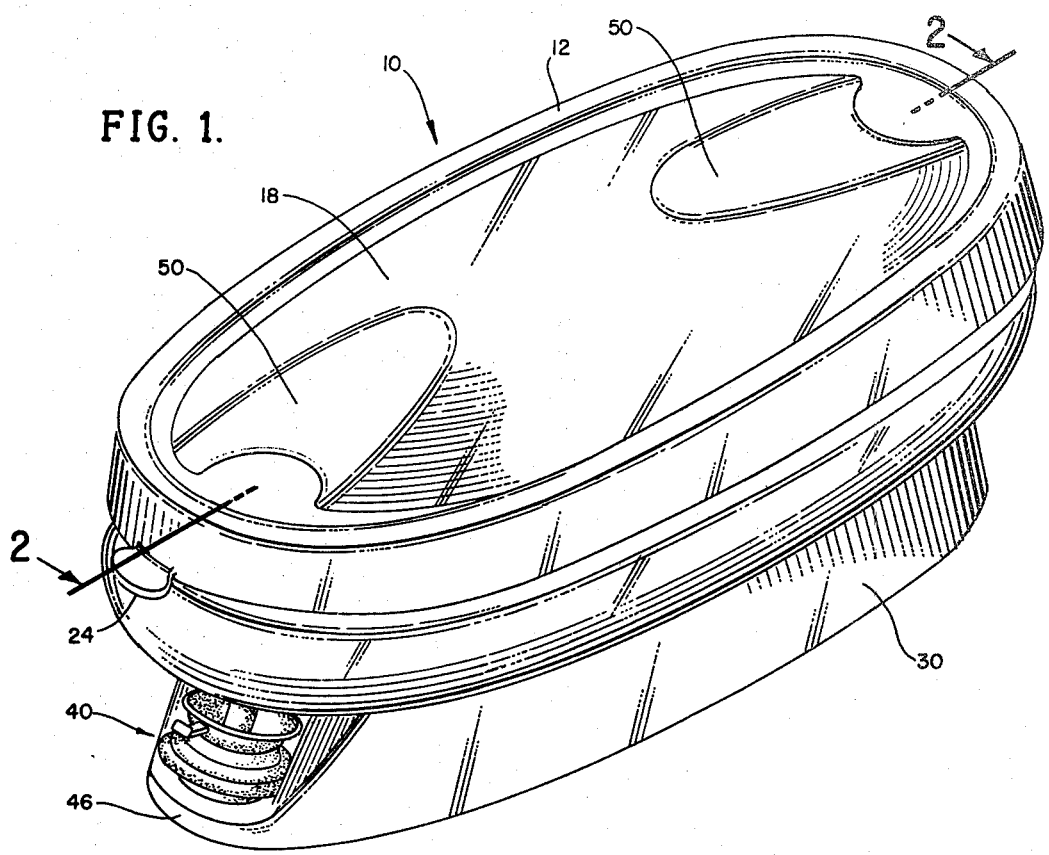
FIG. 1 is a perspective view of a container illustrating the invention.
Figure 2:
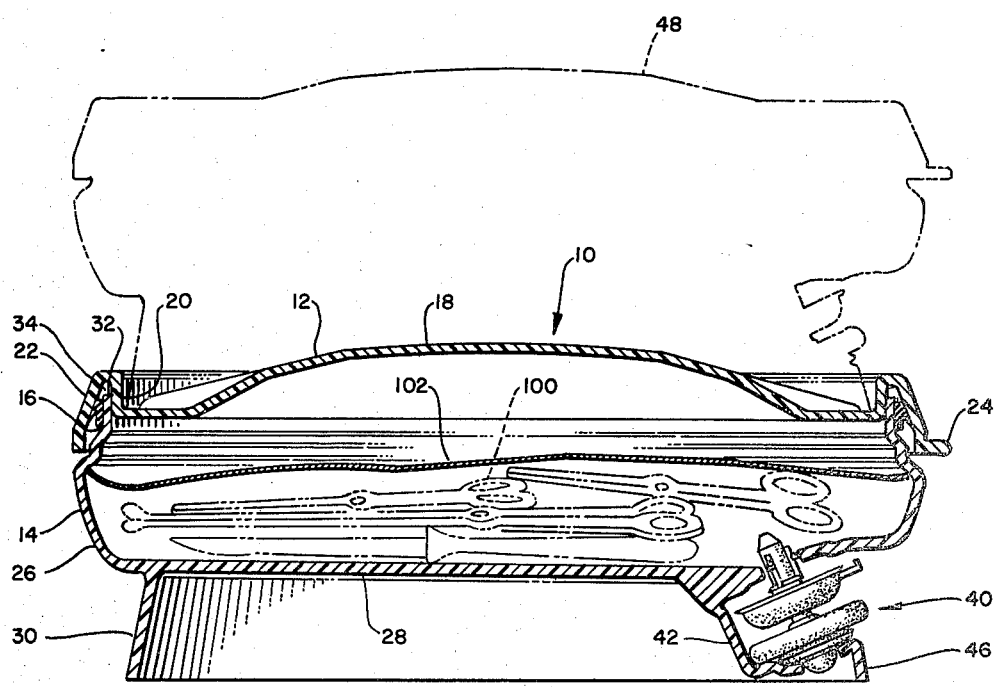
FIG. 2 is a cross-sectional view of the container on lines 2—2 of FIG. 1 illustrating the overall arrangement and the slope of the bottom wall of the container.

Referring now to FIGS. 1 and 2, there is shown a container 10 having a cover or lid 12 closing the open upper side of a base 14 and seated on a gasket 16 extending between the base and the lid. As can be seen, the container has a generally oval or race track configuration and the lid has an upper wall 18 which slopes gradually upwardly towards the center. The purpose for the oval shape and the upwardly curving wall 18 is to provide strength to the container when it is subjected to an exterior pressure considerably higher than the interior pressure. The cover 12 further includes a peripheral flange portion having a generally vertical internal wall 20 which joins at its upper end a downwardly and outwardly sloping flange 22. A tab 24 extends outwardly from the bottom of the flange 22 at one end of the container.

The base 14 includes an irregular but generally upwardly extending side wall 26 formed integral with a bottom wall 28 and a downwardly extending peripheral leg structure 30. The side wall 26 terminates at its upper end with a short vertically extending portion 32 which extends into the downwardly extending groove 34 formed by the inner surface of the lid flange 22 and the outer surface of the lid wall 20. As can be seen from FIG. 2, the lid wall 20 fits within the upper end of the base wall 32. The portion of the side wall 26 below the upper portion 32 extends outwardly to a point where the lower portion of the wall 26 generally aligns with or forms an extension of the exterior surface of the lid flange 22.

The gasket 16 is made of flexible rubber-like material which can withstand the temperature of an autoclave operation and yet provide an adequate seal. The gasket 16 includes an inner vertical portion which fits snuggly around a groove in the wall 32 on the upper end of the base side wall 26. The gasket 16 further includes a downwardly and outwardly extending flange portion which mates with the inner surface of the lid flange 22.

The bottom wall 28 of the base slopes generally toward a valve opening 36 in the right end of the base as viewed in FIG. 2. The base leg 30 extends inwardly at the right end of the base to form a recess 38 in which is positioned a valve and valve closing assembly 40 which cooperates with the valve opening 36. More specifically, the recess 38 is formed by a sloping leg wall 42 which extends in a generally cylindrical configuration about 180 degrees to partially enclose the valve and valve closing assembly 38. The wall 42 is further connected to a bottom support wall 44 which extends generally perpendicular to the side wall 42 and joins with a stub leg wall 46 on the periphery of the base leg. A hole 41 is formed in the bottom wall 44 for positioning the assembly 40.

As can be seen by the broken lines in FIG. 2, a second container 48 may be stacked on the lower container 10 with the leg of the upper container being positioned on the lid 12 in the groove formed by the lid side wall 20 and by the outer periphery of the lid upper wall 18. As seen from FIG. 1, each end of the lid has a shallow recess 50 adapted to receive the wall portions 44 and 42 of the upper container 48. A recess 50 is formed on each end of the lid so that the user need not worry about orientation of the container 48 when it is being stacked on the container 10. Naturally more than two containers may be stacked if desired.

Referring now to FIGS. 3 and 4, the valve and closing mechanism 40 may be seen to include a valve 52 which is a flexible resilient member molded of silicone rubber or other rubber-like material which can withstand steam temperatures while maintaining its resiliency. The valve includes a base 54 which when unrestrained has a generally saucer shaped configuration with the upper surface of the base 54 forming the sealing surface against the container when the valve is closed. Attached to the central portion of the base 54 is an upwardly extending generally cylindrical stem or core 56. As may be seen from FIG. 4 and 6, much of the core 56 is hollow opening to the lower side of the base 54. The upper end of the core 56 extends through the opening 36 in the container lower wall, the end 57 of the core 56 having a solid conical shape to facilitate insertion of the core into the opening 36. The portion of the core 56 actually extending through the opening 36 as viewed in FIG. 4 includes three radially extending circumferentially spaced ribs 58. Each rib further has a radially extending lug 60 which has a tapered upper surface 60a which engages the lower edge of the opening 36 with the assembly positioned as shown in FIG. 4.

A tab 62 extends radially outwardly from one edge of the valve member base 54 to form a convenient element for removing the valve member from the valve opening 36.

The assembly 40 further includes a valve closing means comprising a generally disc-shaped hollow member 64 which is made of flexible rubber-like material and defines an expandable interior chamber 66. Since the member 64 is flexible and stretchable, it might be thought of as a ballon or bellos-like member. The bottom side of member 64 includes a centrally located thickened throat 68 which defines a circular opening into the chamber 66. A circular plug 70 snaps within the throat 68 in the lower wall of the member 64. More specifically, the plug 70 includes a side wall 72 which slopes downwardly and outwardly and is slightly larger in diameter than the throat 68. A side wall 72 further includes an outwardly extending flange 74 that forms a continuation of the upper wall 76 of the plug. The throat 68 snuggly engages the side wall 72 of the plug and the flange 74 snuggly engages the lower wall of the chamber 66 surrounding the throat 68. While the plug 70 snaps into position in the throat 68 to close the chamber 66, there is further provided a resilient ring shaped retaining element 77, which surrounds the exterior of the throat 68 holding it in tight engagement with the plug side wall 72.

The plug 70 further includes a lower guide portion 78 having a curved exterior which fits within an opening 41 in the container wall portion 44 which supports the valve and valve actuating assembly 40.

A valve passage 82 extends centrally through the plug from the lower portion 78 and upwardly into a tubular portion 84 that extends above the upper wall 76. The upper end of the tube 84 is closed by a plate or wall 86. A hole 88 extends radially through the tube 84 to place the chamber 66 in fluid communication with the atmosphere around the assembly 40.

Formed in the upper wall 76 of the plug 70 is an annular recess or groove 90 in which is positioned a thin band 92 which surrounds the tube 84 and extends over the valve opening 88. The band 92 is made of heat shrinkable material which shrinks and becomes permanently rigid at a predetermined temperature.

The balloon member 64 further includes an upwardly extending nipple 94 which snuggly fits within the cylindrical recess 55 in the lower wall of the valve base 54 as seen in FIG. 4. The interior of the nipple 94 is hollow and is open to the chamber 66 when the chamber is expanded; however, in the position of FIG. 4, the upper wall 86 of the tube 84 of the plug 70 engages the lower end of the nipple 94 and thereby limits the contraction of the chamber 66. Loosely surrounding the nipple 94 is a heat shrinkable band 96.

Operation

Referring to FIG. 2, the container lid 12 is removed and the articles 100 to be sterilized are placed within the base 14. They are then loosely covered by a thin sheet of transparent plastic material 102 which can withstand sterilizing steam temperatures. The lid 12 is then loosely placed in position on the base 14 with the interior of the inner surface of the flange 16 engaging the outer surface of the flexible gasket 22. In this position the lid or cover is closed in the sense that air cannot flow into the container passed the gasket but the cover is not fully closed onto the base.

A valve and valve closing assembly 40 is positioned within the recess 38 as shown in FIGS. 2 and 4. The components of the assembly 40 are usually provided in an assembled condition wherein the band 96 is first loosely positioned on the nipple 94 of the valve actuating member 64 and the nipple is then pressed into the recess 55 in the lower end of the valve member. The valve is retained in this position by a slight friction fit. The assembly 40 is therefore inserted into the recess 38 as a unit. Since the components are flexible, the upper end 57 of the valve core may be easily inserted into the container valve opening 36, allowing the lower end of the valve actuating member 64 to be snapped into position. The lower surface 78 of the core 70 conforms to the hole 41 in the container support wall 44 to properly align the assembly. The alignment ribs 58 on the valve core 56 properly align the valve with respect to the hole 36. Also, the outwardly extending lugs 60 limit the inward movement of the valve to tell the user of the equipment that the assembly is properly positioned. The tolerance of the components are relatively loose but yet the design is such that precise alignment is not critical to obtain proper seating of the valve.

Figure 8:
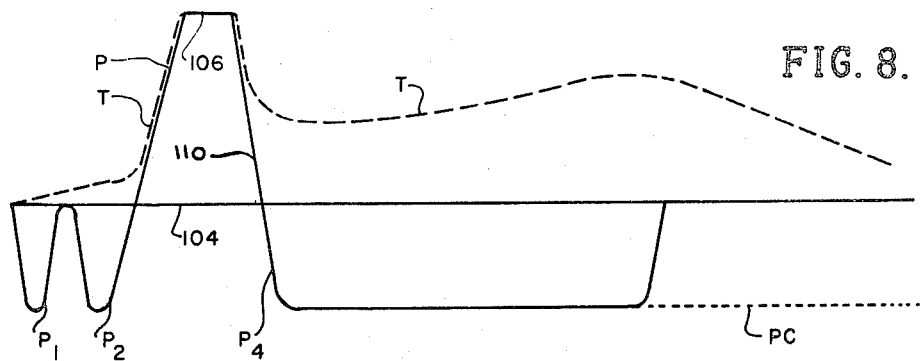
FIG. 8 is a schematic illustration of a vacuum autoclave cycle indicating the points on the pressure and temperature curves at which the operation of the mechanism curves.

The valve closing assembly is primarly designed for use in a sterilizing apparatus which includes a high pressure steam cycle. Two widely used sterilizers are the so-called gravity autoclave and the vacuum autoclave. An example of the pressure and temperature cycles in one type of vacuum autoclave is illustrated in FIG. 8. The horizontal line 104 respresents time. T represents a temperature curve and P represents the pressure curve, with the line 104 indicating normal room temperature and pressure. When the container 10 is placed within the vacuum autoclave, a first vacuum environment indicated by the section T1 of the pressure curve is first applied. Most of the unsterilized air within the autoclave is withdrawn as is the air within the container 10 since the interior of the container is in communication with the interior of the autoclave by means of the valve opening 36 in the bottom wall of the container. The pressure within the autoclave is then once more allowed to return to ambient pressure by allowing steam into the chamber. A second vacuum cycle P2 on the pressure curve shown on FIG. 8 is then applied which withdraws the steam within the autoclave which has mixed with the small amount of remaining unsterile air. In some sterilizers, additional vacuum cycles of this type are employed.

High pressure steam is then introduced into the autoclave causing the pressure as well as the temperature to rise as indicated by the curves T and P. The temperature and pressure curves are shown coincident at this time in that they both rise at the same time and the units of measurement employed are assumed to cause the curves to move in a coincident manner. It should be understood that this is not intended to be a precise showing of the actual curves but only to illustrate that the temperature and pressure are both rising to their maximum levels during this phase. The high temperature steam of course circulates into the interior of the container by way of the valve opening 36. Also, the high pressure high temperature steam also circulates into the chamber 66 by way of the valve passage 82 and the valve opening 88, noting that the cylindrical valve element 92 is spaced from the opening 88 to permit such flow. Note that even if the valve band 92 is positioned loosely over the opening 88, the pressure differential between the chamber 66 and the surrounding autoclave pressure causes the steam to flow into the chamber 66.

When the temperatures and pressures are near their maximum, the heat of the steam causes the heat shrinkable sleeve 92 to shrink to its position shown in FIG. 5 wherein it closes the opening 88, thereby capturing a volume of high pressure high temperature steam within the chamber 66. This point 106 is shown in FIG. 8.

The steaming cycle continues for a desired period of time. Most autoclaves are adjustable to vary the duration of the steaming portion. The graph shown in FIG. 8 illustrates the steaming cycle to be of relatively short duration; howwever, the duration should be adjusted to fit the load within the container. A load requiring a particularly long period of time is one which includes a large quantity of metal elements having considerable mass. For example, a larger quantity of surgical tools would have considerable mass. Even more demanding, during the testing of the container, a load of steel bolts were placed in the unit. Such a load requires a considerable period of time for adequate sterilizing in that it takes a considerable quantity of steam to heat the entire mass of the load to the desired sterilizing temperature. The surface of the heavy metal items will remain relatively cool until the interior of the items are heated because of the conductivity of the material. As the hot steam strikes the cooler metal, some of the steam condenses and drips onto the floor or bottom wall 28 of the container. Although this liquid would be sterile at the end of a sterilizing cycle, it is desirable that the water be removed from the container so that the container will be as dry as possible during storage. It is for this reason that the bottom wall 28 of the container is slightly sloped so that the water will flow towards and out the opening 36. Regardless of the length of the steaming cycle, the valve 36 will remain open in that there is no force for closing it. However, when the steaming cycle is interrupted, the pressure quickly drops as illustrated by the section P3 of the curve. A final vacuum cycle is then applied to withdraw the steam as indicated by the curve section P4. Following this, the vacuum is removed by allowing the introduction of filtered exterior air so that the pressure within the autoclave returns to room pressure.

As the pressure in the autoclave is dropping from its maximum, the captured pressure within the chamber 66 causes the balloon 64 to expand. Since the pressure drops rapidly into a vacuum phase, the balloon 64 expands quickly into the condition shown in FIG. 5 wherein the nipple portion 94 may be seen to have moved upwardly a considerable distance thrusting the valve member 54 against the annular valve seat 37 surrounding the valve opening 36. As can be seen from FIG. 5, a large portion of the inner upper surface of the flexible resilient base portion 54 of the valve engages the valve seat 37 to form an excellent seal. Note also that the valve seat 37 has a concave configuration or curves inwardly towards the interior of the container and that the valve member conforms to the valve seat surface. The exact point of closure of the valve is not critical but the valve will typically close in the area indicated by the point 110 on the pressure curve in FIG. 8.

It should be noted from FIG. 5 that the balloon member 64 is constructed to insure its expansion into the configuration illustrated. That is, the outer edge walls of the member 64 are somewhat thicker then some of the adjacent portions so that the balloon does not expand radially. Also, the upper wall of the member 64 includes a thickened annular rib portion which causes the balloon to take the general configuration illustrated which insures that adequate upward thrust of the valve closing member is obtained.

It should also be noted that sufficient thrust is required to force the lugs 60a on the valve core 56 through the opening 36. The purpose for these lugs in addition to initially properly positioning the valve is to make sure that the valve does not close prematurely due to a temporary drop in the pressure of the steaming cycle. That is, it has been found that some autoclaves have a considerable pressure variation as the steam is fed through the unit. Thus, a drop in pressure in the middle of the steam phase could cause the valve to close. However, the presence of the lugs 60 requires a sufficient force that nominal variations in the steam pressure will not close the valve. About a 10 psi pressure drop is required to close the valve.

Although the container is now closed by virtue of the valve 54 and the gasket 16, recall that the lid 12 was initially only loosely positioned on the base. Thus, as the pressure drops during phases P3 and P4 of the pressure cycle, a pressure differential between the interior and the exterior of the container is initiated. However, a unique quality of the gasket is that it will permit leakage out of the container with a relatively small pressure differential. Consequently, the steam that was within the container when the valve closed is still withdrawn from the container by the vacuum cycle. This is highly desirable because it means that the contents of the container are left in a dry and sterile condition. Thus, even at the bottom of the vacuum cycle, the lid 12 is still only loosely positioned on the gasket 16. Nevertheless, the flexible resilient nature of the gasket is such that gas cannot flow into the continer. Thus, the gasket during this phase of the cycle essentially acts like a check valve.

When external filtered air is introduced into the autoclave allowing the pressure to return to ambient, the vacuum which was applied to the autoclave still remains within the container, as indicated by the dotted line PC. The gasket 16 and the valve 54 prevent this external air from entering the container. Although such air is filtered it is nevertheless not sterilized and hence, it is important that this air not enter the container to best maintain sterility.

Since the incoming air cannot enter the container, the pressure of this air quickly forces the lid downwardly into its maximum closed position with the lid flange 22 tightly pressed against the gasket 16 so as to more positively prevent external air from entering the container. Similarly, the exterior air presses against the valve member 54 causing it to remain tightly seated on the valve seat 37 as illustrated in FIG. 6.

Referring again to FIG. 8, the temperature in the autoclave also drops rapidly once the steaming cycle is interrupted, but then remains at an elevated level and slightly rises during the final vacuum phase, since the autoclave is heated. When the container is removed from the autoclave, the temperature gradually returns to normal. The reduction in temperature within the autoclave and later outside the autoclave eventually also cools the steam within the balloon chamber 66 causing a reduction in pressure within the chamber 66. This causes the resilient balloon member 64 to contract and revert to a position close to that it originally assumed, as illustrated in FIG. 6. The valve member 54 is of course no longer supported by the balloon 64 in that the ambient pressure is tightly holding the valve in position without any other support. This force is so strong that the weight of the inflatable chamber members 64 and 70 is of no consequence with respect to the seal produced by the valve, but usually the enlargement of the valve recess 55 results in the members following and returning to the position shown in FIG. 6. However, if the friction between the nipple 94 and the tubular recess 55 is sufficient, the valve closing member will be lifted from its seat resting on the support wall 44. The valve closing member may remain in either of these two positions or it may be withdrawn or recycled for an additional use. It can of course, not be reused unless the plug 70 is withdrawn from the flexible member 64 and the heat shrink band 92 removed so that the valve opening 88 once more permits communication between the chamber 66 and the exterior. By providing a new heat shrink band 92, the valve closing member can be reused. Normally, such recycling will be performed by people other than those using the container.

Figure 6:
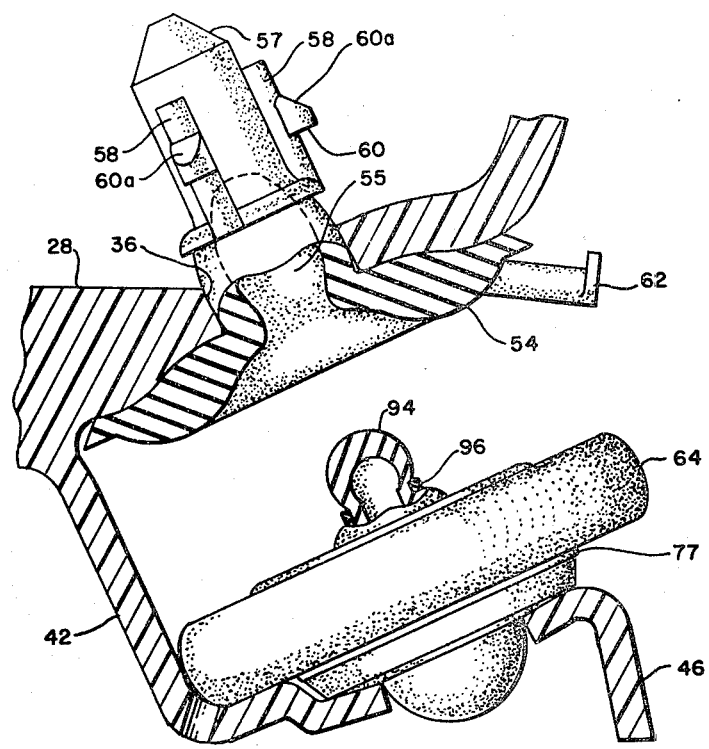
FIG. 6 is a cross-sectional view of the structure of FIG. 4 showing the valve held in place by pressure on the exterior of the container and showing the expandable chamber in retracted position.

Note from FIG. 6 that the heat shrink band 96 has shrunk tightly onto the nipple 94 because of the high temperature steam. This band 96 is colored differently from the nipple 94 to provide an indication to the user of the container that the valve moving member has been used. Thus, this indicator band should be removed when the internal heat shrink valve element is replaced. A new indicator band should be loosely positioned over the nipple when it is inserted in a valve which is to be reused.

Figure 7:
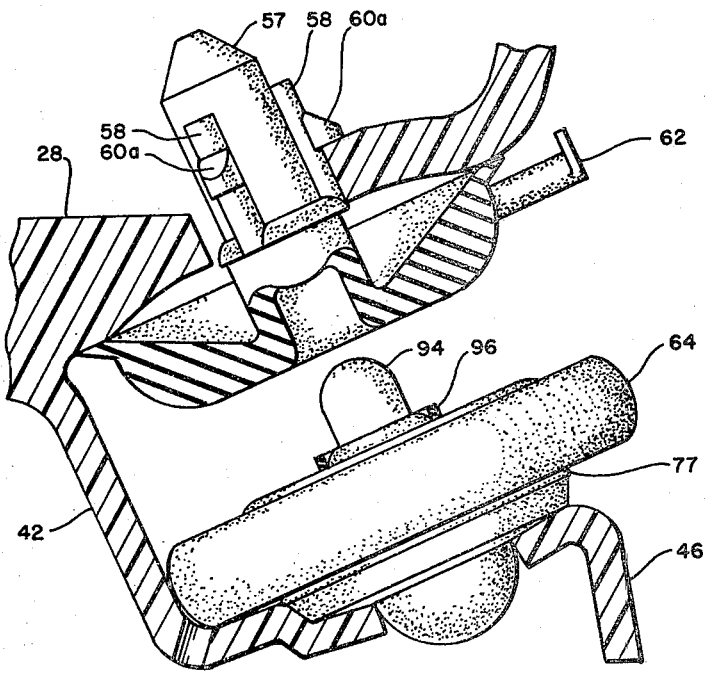
FIG. 7 is a cross-sectional view of the structure of FIG. 4 as it appears after the valve has been placed in position by the expandable chamber near the end of the steaming phase of a gravity autoclave, but before the valve is tightly drawn into sealing position on the container valve seat by the vacuum created in the container as it cools.

With the valve member closing the opening in the end of the container, the contents of the container may be maintained in sterile condition for a long period of time. So long as the valve is in the position shown in FIG. 6, an observer will know that the contents are still sterile. If the vacuum within the container should be lost, the valve will withdraw slightly from the tightly sealed position due to the weight of the valve and its memory. This will tell the observer that the contents may no longer be of maximum sterility. However, the lugs 60 on the valve core 56 continue to hold the valve in the sealed position shwn in FIG. 7. While such seal has permitted some air to enter the container as the vacuum was lost, the contents still have a minumum amount of contamination, and it is much less than that which relatively quickly results with present day methods of wrapping items to be sterilized and stored in towels.

When the container is to be opened and the valve is still tightly sealed as shown in FIG. 6, the valve member may be readily removed by pulling on the tab 62 attached to the valve member. As mentioned above, the valve member can be reused if desired, assuming it has not been held in a valve closed position so long that the material no longer has adequate resiliency to maintain its original shape.

The container cover may then be removed, although it may still be somewhat tightly in position even though the vacuum has been removed. To facilitate removal of the cover, the base may be held with one hand and the cover lifted by means of the tab 24 located on one end of the cover.

Normally, the container will have been removed from a storage location into the operating area before it is opened. When the cover is removed, there is a possibility that some dust or other contamination that may have accumulated on the exterior of the cover during storage could drop into the container interior. It is for this reason that the additional barrier layer of flexible plastic 102 was installed over the instruments prior to the sterilizing operation. This barrier layer can now be carefully removed by grasping one end and withdrawing it over one edge of the container so that hopefully any dust that may have fallen into the container will be removed with the barrier layer, or at least such dust will not fall directly onto the sterile instruments.

Gravity Autoclave Operation

Figure 9:
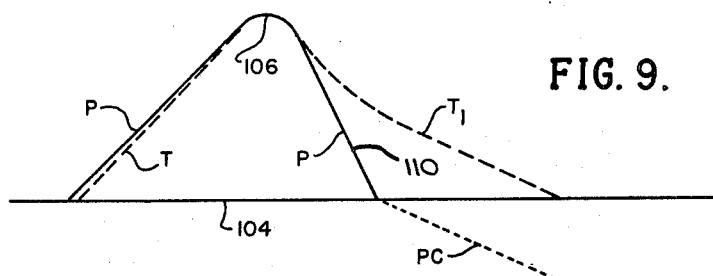
FIG. 9 is a sketch similar to FIG. 8 but for a gravity autoclave.
Figure 10:
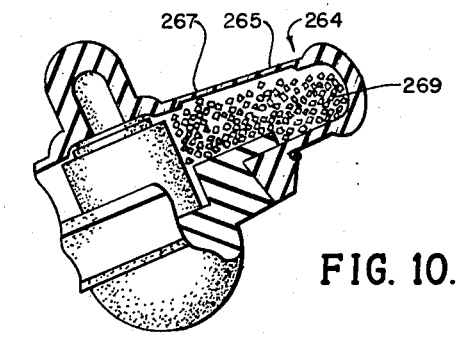
FIG. 10 is a fragmentary view showing a variation of the expandable chamber serving as a dessicant bag.

While a vacuum autoclave sterilizing cycle is preferable from a standpoint of sterility and from a standpoint of best operation of this container, a large number of gravity autoclaves are still employed and the valve and valve closing assembly 40 of this invention can accommodate such cycle as well. Referring to FIG. 9 it may be seen that there are no vacuum cycles applied but instead high pressure steam is simply applied and then withdrawn. The valve and valve closing assembly 40 is used in the same manner as described above in connection with the vacuum cycle. The valve member 54 is closed at approximately the same location 110 on the pressure curve. Also, as the pressure is exhausted from the autoclave, pressure is exhausted from the container passed the gasket in the same manner as described above. However, the only means for creating a vacuum within the container which will draw the lid more tightly into closed position and will hold the valve member 54 in tightly sealed condition is that vacuum which is created as the temperature of the small amount of residual steam within the container drops. The vacuum created in the container will follow a line more proportional to the temperature curve indicated at T1 in FIG. 9. Thus, for a period of time, there may be insufficient pressure differential to hold the valve member 54 in the tightly sealed position shown in FIG. 6. Instead, it may temporarily drop to the position shown in FIG. 7 wherein the lugs 60 retain the valve member in a sealing condition which prevents air leakage into the container. Note that the outer periphery of the valve member is oriented to properly engage the valve seat in that condition to prevent leakage into the container.

As the temperature of the residual steam within the container drops further, an adequate pressure differential is created which will force the valve member back into the tightly sealed condition of FIG. 6. Also, it will pull the lid tightly into a sealed position on the gasket 16. The pressure within the container is indicated by the dotted line PC in FIG. 9. It should be appreciated that a relatively high vacuum is obtained even with the gravity type autoclave simply due to the pressure drop which is created as the residual steam condenses. While it is desirable that the contents of the container be completely dry, a small amount of sterile water, such as a few drops within the container does not present a significant problem.

Figure 12:
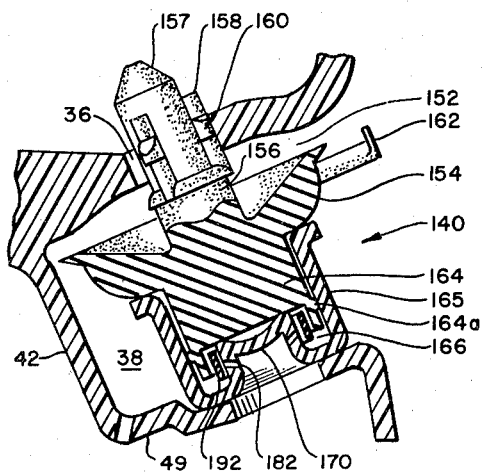
FIG. 12 is a cross-sectional view of a piston type expandable chamber valve closing mechanism shown before the chamber has expanded to seat the valve.

However, to keep such moisture away from the items in the container, a small amount of dessicant or other moisture absorbing material may be positioned in the container, with suitable means to isolate the dessicant until the end of the cycle. Such an arrangement is shown in FIG. 12 which illustrates an expandable balloon member 264 which is identical to the member 64 in FIG. 4 except that the upper wall 265 has a breakable or rupturable portion 267 which is much thinner than the adjacent wall thickness. The chamber within the member 264 is filled with dessicant which is exposed to the interior of the container at the appropriate time to absorb residual moisture. In use, the inflatable member 264 is filled with a suitable dry dessicant 268 in granule form, which leaves a quantity of air in the chamber surrounding the granules. A plug 70 carrying a heat shrink band 92 like that shown in FIG. 4 is then inserted in the lower wall of the inflatable member 264 in the manner discussed above. The unit is then heated in an oven to sterilize the dessicant and to sterilize the interior of the inflatable member 264. During this heating process, the heat shrink tube 92 will shrink and close the valve opening leading to the interior of the inflatable member 264, capturing a small volume of air that was in the oven. The proper time for sterilization at a given temperature is allowed. The member is then cooled and in effect becomes a small dessicant bomb which will rupture under the proper pressure conditions.

When the container 10 of FIG. 1 is to be used in a gravity autoclave, one of the sealed members 264 filled with dessicant 269 is placed into the container along with the items to be sterilized. When the sterilizing environment is applied to the container, it can not enter the dessicant bomb 269 because it is sealed. However, at the end of the sterilizing cycle, when a vacuum is quickly created in the container as the residual steam in the container is cooled and condenses, the pressure is not reduced as quickly within the member 264 because the air in the member remains gaseous. Consequently, the member inflates or expands as the surrounding pressure within the container falls and the thin wall section 265 will rupture exposing the dessicant to the interior of the container.

Figure 11:
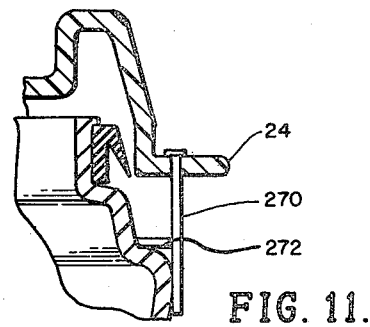
FIG. 11 is a fragmentary view showing another variation wherein the lid of a container is initially held open.

Another aspect of using the container in a gravity autoclave is that the container is initially filled with unsterilized air when it is placed in the autoclave. When steam is applied, it mixes with the air and sterilizes it. However, there is some possibility that a pocket of air may be trapped within the container near the end of the container opposite from the valve opening in that the air is heavier than the steam and circulation may not be complete simply by having the valve open. Thus, as a further assist to adequate circulation, there is shown in FIG. 11 the end of the container opposite the valve assembly wherein a heat responsive fuse-like element 270 is shown holding the lid 12 spaced slightly from the base 14. The element 270 is inserted in a hole in the lid tab 24 with an interference fit in a manner to be axially fixed and supported by the lid. A horizontally extending stop 272 on the element 270 and the lower end of the element 270 engage the side wall of the base to hold the lid in the spaced position shown. The element 270 is made of a material which will soften after being subjected to the high temperature steam for a predetermined period of time. Thus, the lid is partially open when steam is first applied with the result that the steam can circulate beneath the lid into the container displacing the air in the container out through the open valve in the bottom of the container. When the element 270 softens, the lid simply falls into its initially closed position as discussed above in connection with FIG. 2; and the remainder of the cycle is as previously discussed. Other similar fuse-like arrangements may be employed for temporarily holding the lid ajar.

FIGS. 12 AND 13

Figure 13:
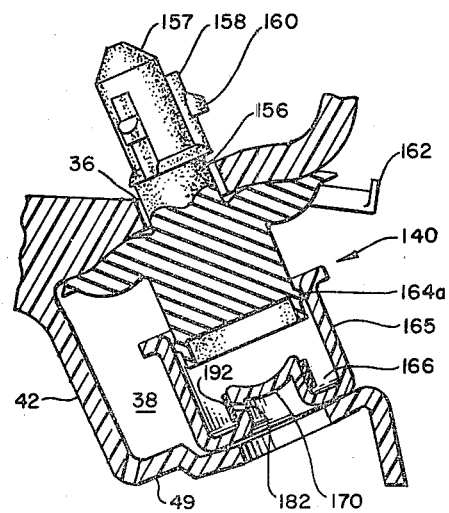
FIG. 13 is an elevational view of the structure of FIG. 12 showing the components after the valve has seated.

FIGS. 12 and 13 illustrate an alternate embodiment of the valve and valve closure mechanism as used in an identical container. Referring to FIG. 12 there is shown a valve and valve closure assembly 140 which includes a valve 152 having a saucer shaped base 154 and a centrally located upwardly extending core or stem 156 having a conical tip 157. Like the valve 52, the core 156 is provided with three ribs 158 having radially extending lugs 160. A tab 162 is formed integral with the base 154 for removing the valve from the valve opening 36.

Also formed integral with the valve base 154 is a cylindrical portion which forms a piston 164. This piston is slidably positioned within a cup shaped member 165 defining a variable or expandable chamber 166 in cooperation with the piston 164. An annular bead 164a on the lower end of the piston engages the walls of the cylinder 165 to form a piston ring.

The cup shaped cylinder has a centrally located inwardly extending portion 170 which limits the movement of the piston 164 into the cylinder 165. One or more valve openings 182 place the chamber 166 in fluid communication with the exterior of the chamber. Surrounding the central portion 170 and the valve openings 182 is a heat shrink band 192 similar to that shown in FIG. 4. As seen in FIG. 12, the band is spaced from the valve openings 182 so that fluid communication into the chamber 166 is maintained.

In operation, the assembly 140 functions essentially like the assembly 40 previously described. The heat band 192 shrinks at a predetermined temperature level indicated at point 106 on the curves in FIGS. 8 and 9. Thus, a quantity of high temperature, high pressure steam is captured within the chamber 166. When the pressure drops within the autoclave, the captured steam in the chamber 166 expands and reacts against the piston 164, forcing it upwardly and outwardly so that the valve 154 is sealed on the valve seat 37 as shown in FIG. 13. As the vacuum is created in the container in the manner discussed above in connection with the two sterilizing cycles, the resulting pressure differential will hold the valve in the seated position shown in FIG. 13.

With the arrangement of FIG. 13 it is intended that the cylinder 165 remain with the container in the position shown. When the container contents are to be used, the valve 152 may be removed in the same manner as the valve 52 namely by pulling on the tab 162.

It should be understood that with either expandable chamber mechanism, a simple check valve is satisfactory for capturing steam in the chamber means for use in a gravity autoclave. Such a valve will permit flow into the expandable chamber but not out. The temperature responsive valve is employed so that in a vacuum autoclave cycle the chamber does not expand during either of the initial vacuum cycles. The heat shrink bands 92 and 192 actually function as check valves after they initially shrink in that the material is rubber-like at that time. However, when the material later cools, it becomes permanently rigid.

FIGS. 14 AND 15

Figure 14:
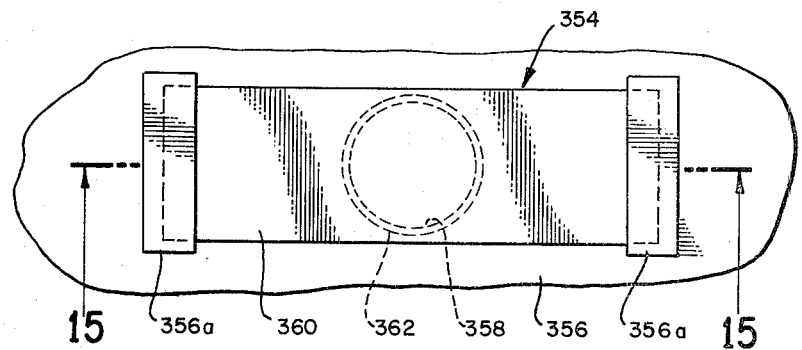
FIG. 14 is another container valve arrangement illustrating the invention.
Figure 15:
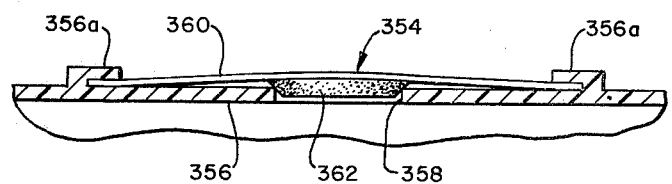
FIG. 15 is a cross-sectional view on line 14—14 of FIG. 14.

FIGS. 14 and 15 illustrate a valve assembly 354 positioned in the wall 356 of a container such as that shown in FIG. 1. This valve assembly performs some of the same functions as the assembly 40 in FIG. 1. The valve assembly may be positioned in the lid or whatever other wall of the container is desired; but to have the drainage feature referred to above, it is necessary to position the valve in the bottom wall of the container.

A hole 358, as shown in FIG. 15, is formed in the container wall 356 with a pair of spaced lugs 356a being attached to or formed integral with the wall 356 straddling the hole 358. A bimetallic element 360 extends over the hole with the ends of the element being confined by the lugs 356a. A resilient valve member 362 is attached to the central portion of the bimetallic element aligned with the hole 356. The bimetallic element 360 is selected so that it holds the valve member 358 in closed position at normal room temperatures and well above such temperatures. However, when the bimetallic element is heated to a predetermined temperature, such as by the application of steam in an autoclave, it moves to a position wherein a valve member 362 is spaced from the hole 358 so that the valve is open and permits the steam to enter the container. The valve will remain open during the steaming phase of a sterilizing cycle in an autoclave regardless of the length of that phase. When the steaming phase is over and the temperature drops below sterilizing temperatures, but is still well above normal room temperature, the bimetallic element 360 flexes to move the valve member 362 into the closed position shown in FIG. 14.

The temperature at which the bimetallic valve closes need not be particularly precise, but it is important that it close before unsterile room air is allowed to enter the autoclave. When the bimetallic valve 354 is used in a vacuum autoclave, the valve is normally closed when the final vacuum is applied. Thus, in referring to FIG. 8, the valve would close above the broken temperature line T which occurs during the final vacuum. This insures that the valve is closed when room air is admitted to the autoclave to relieve the vacuum. Although such air is normally filtered, it has not been sterilized by heat. Although the valve is closed when the final vacuum is applied, the spring characteristics of the bimetallic element 360 make it pressure responsive and permit the valve member 362 to be drawn slightly open by the vacuum to enable the vapor within the container to be withdrawn. When the pressure on the interior moves closer to that on the exterior, the valve will close again.

Thus, the valve assembly 354 is similar to assembly 40 in that (1) it remains open throughout the steaming phase of an autoclave cycle; (2) it closes automatically in response to a condition of the sterilizing environment before the container is exposed to unsterile air; and (3) it is pressure responsive to open and permit vapor withdrawl when a vacuum is applied. On the other hand, the assembly 354 is temperature responsive to open and close the valve before and after the steaming phase, and the assembly 40 is activated by temperature and thereafter responsive to gaseous pressure to close the valve. Gaseous pressure, of course, varies with temperature.

What is claimed is:

1. Apparatus for containing items while being sterilized or stored comprising:
    means defining a container;
    means in a wall of the container for permitting access to the container interior; and
    means responsive to a sterilizing environment applied to the container interior and exterior to close said container access means after its contents have been sterilized to prevent further environment from entering the container after sterilization, said container being constructed so that further environment cannot enter the container after said access means is closed;
    said responsive means including pressure responsive means for permitting said sterilizing environment to escape from said container when the gaseous pressure in the container exceeds the pressure outside the container a slight amount;
    said means responsive to the sterilizing environment including a temperature responsive valve which closes automatically after said items have been subjected to a sterilizing temperature long enough to sterilize said items, and said valve being also constructed to serve as a pressure responsive check valve and form the means for permitting said environment to escape from the container.

* * * * *